US00PP14163P29

(12) United States Plant Patent
Karmelk

(10) Patent No.: US PP14,163 P2
(45) Date of Patent: Sep. 23, 2003

(54) LAVATERA PLANT NAMED 'BARNSLEY BABY'

(75) Inventor: Wilko Karmelk, Overslag (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/139,957

(22) Filed: May 6, 2002

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Lavatera plant named 'Barnsley Baby', characterized by its upright, outwardly spreading and relatively short plant habit; freely flowering habit; and white-colored flowers with red purple-colored centers.

1 Drawing Sheet

Botanical classification/cultivar designation: *Lavatera L.* cultivar Barnsley Baby.

BACKGROUND OF THE INVENTION

The present Invention relates to a new and distinct cultivar of Lavatera plant, botanically known as *Lavatera L.,* and hereinafter referred to by the cultivar name Barnsley Baby.

The new Lavatera originated from a chance cross-pollination of two unidentified selections of *Lavatera L.,* not patented. The new Lavatera was discovered by the Inventor in 1998 in Overslag, The Netherlands. Plants of the new Lavatera differed primarily from plants of the unidentified parental selections in plant size and flower color.

Asexual reproduction of the new cultivar by cuttings in Overslag, The Netherlands since 1998, has shown that the unique features of this new Lavatera are stable and reproduced true to type in successive generations.

SUMMARY OF THE INVENTION

Plants of the cultivar Barnsley Baby have not been observed under all possible environmental and cultural conditions. The phenotype may vary somewhat with variations in environment such as temperature, light intensity, daylength, irrigation amount and frequency, and/or fertilizer rate without, however, any variance in genotype.

The following traits have been repeatedly observed and are determined to be the unique characteristics of 'Barnsley Baby'. These characteristics in combination distinguish 'Barnsley Baby' as a new and distinct cultivar:

1. Upright, outwardly spreading and relatively short plant habit.
2. Freely flowering habit.
3. White-colored flowers with red purple-colored centers.

Plants of the new Lavatera can be compared to plants of the Lavatera cultivar Barnsley, not patented. In side-by-side comparisons conducted in Overslag, The Netherlands, plants of the new Lavatera differed from of the cultivar Barnsley in the following characteristics:

1. Plants of the new Lavatera were much shorter than plants of the cultivar Barnsley.
2. Plants of the new Lavatera had darker colored stems than plants of the cultivar Barnsley.

BRIEF DESCRIPTION OF THE PHOTOGRAPH

The accompanying colored photograph illustrates the overall appearance of the new Lavatera, showing the colors as true as it is reasonably possible to obtain in colored reproductions of this type. Colors in the photograph may differ slightly from the color values cited in the detailed botanical description which accurately describe the colors of the new Lavatera. The photograph comprises a side perspective view of a typical two-year old flowering plant of 'Barnsley Baby'.

DETAILED BOTANICAL DESCRIPTION

In the following description, color references are made to The Royal Horticultural Society Colour Chart, 2001 Edition, except where general terms of ordinary dictionary significance are used. Plants used for the following description were about two years old and grown under outdoor field conditions which closely approximate commercial production conditions in Overslag, The Netherlands. The photograph and the description information were taken in September, 2001.

Botanical classification: *Lavatera L.* cultivar Barnsley Baby.
Parentage: Cross-pollination of two unidentified selections of *Lavatera L.,* not patented.
Propagation:
- *Type.*—By cuttings.
- *Time to initiate roots.*—About 60 days at 18 to 20° C.
- *Time to produce a rooted young plant.*—About 90 days at 20° C.
- *Root description.*—Thick, somewhat fleshy, white to light brown in color.

Plant description:
- *Form.*—Perennial flowering shrub; upright and outwardly spreading plant habit; freely branching; moderately vigorous growth habit.
- *Plant height.*—About 1 meter.
- *Plant diameter.*—About 1 meter.
- *Lateral branch description.*—Number per plant: About 12. Length: About 35 cm. Diameter: About 4 mm. Internode length: About 2.7 cm. Strength: Strong. Texture: Pubescent. Color: 137D overlain with 197A to N220B.

*Foliage description.*—Arrangement: Alternate, simple. Length: About 5.5 cm. Width: About 3.3 cm. Shape: Ovate, lobed. Apex: Very short mucronate. Base: Hastate. Margin: Crenate. Texture, upper and lower surfaces: Pubescent. Venation pattern: Pinnate.

*Petiole.*—Length: About 2.1 cm. Diameter: About 1.5 mm. Texture: Glabrous. Color: Young and fully expanded foliage, upper surface: 137A to 137B. Young and fully expanded foliage, lower surface: 191A. Venation, upper surface: 144B. Venation, lower surface: 191A. Petiole: 137D.

Flower description:

*Appearance.*—Single axillary flowers with five petals. Flowers not persistent. Flowers face mostly outwardly.

*Quantity of flowers.*—About 20 flowers per lateral branch develop during the flowering season.

*Natural flowering season.*—Plants flower continuously from July through September in Overslag, The Netherlands.

*Fragrance.*—None detected.

*Flower longevity.*—About one week.

*Flower diameter.*—About 5.2 cm.

*Flower depth* (*height*).—About 3.7 cm.

*Flower buds.*—Length: About 1.8 cm. Diameter: About 1 cm. Shape: Ovoid. Color: 143C.

*Petals.*—Quantity per flower: Five. Arrangement: Rotate. Length: About 3.5 cm. Width: About 2.7 cm. Shape: Roughly deltoid. Apex: Emarginate. Base: Attenuate. Margin: Entire. Texture, upper and lower surfaces: Smooth, glabrous. Color: When opening and fully opened, upper surface: Closest to 155D; towards base, 63A. When opening and fully opened, lower surface: Closest to 155D; towards base, 61B.

*Sepals.*—Quantity per flower: Five. Arrangement: Rotate. Length: About 1.1 cm. Width: About 5 mm. Shape: Rhomboidal. Apex: Acuminate to aristate. Base: Broadly cuneate, fused. Margin: Entire. Texture, upper and lower surfaces: Pubescent. Color: When opening and fully opened, upper surface: 144B; towards apices, 138B. When opening and fully opened, lower surface: 145A; towards apices, 138B.

*Peduncles.*—Length: About 1.2 cm. Diameter: About 1.2 mm. Angle: About 35 to 50° from vertical. Strength: Strong. Color: 138B.

*Reproductive organs.*—Stamens: Quantity per flower: About 50. Anther shape: Reniform; dorsifixed. Anther length: About 0.8 mm. Anther color: Between 155A and 157D. Pollen amount: Scarce. Pollen color: Close to 155A. Pistils: Quantity per flower: One. Pistil length: About 1.7 cm. Style length: About 1.4 cm. Style color: 64B. Stigma shape: Terete. Stigma color: 63B. Ovary color: 63A.

*Fruit.*—Quantity per plant: About 480. Length: About 1.1 cm. Diameter: About 1.4 cm. Color: 199C to 199D.

*Seed.*—Quantity per fruit: About ten. Length: About 2 mm. Diameter: About 1.5 mm. Color: N200A to N200B.

Disease/pest resistance: Plants of the new Lavatera have not been noted to be resistant to pathogens or pests common to Lavatera.

Temperature tolerance: Plants of the new Lavatera are tolerant to temperatures from about 7 to 40° C.

It is claimed:

1. A new and distinct cultivar of Lavatera plant named 'Barnsley Baby', as illustrated and described.

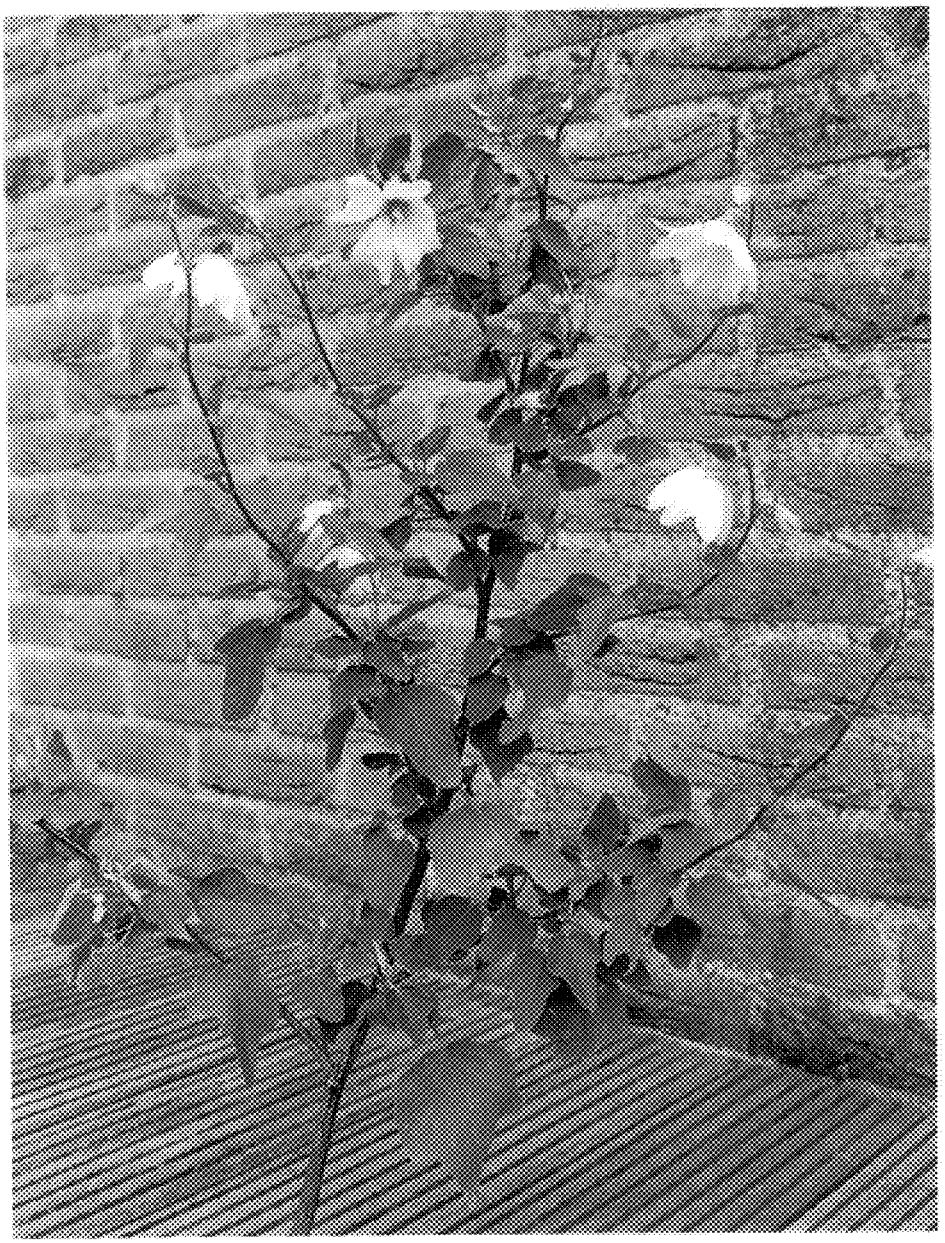

* * * * *